(12) United States Patent
Hundorf et al.

(10) Patent No.: US 9,072,627 B2
(45) Date of Patent: Jul. 7, 2015

(54) APPARATUS AND METHOD FOR RETAINING AND RELEASING SOLID MATERIAL

(75) Inventors: Harald Hermann Hundorf, Bonn (DE); Marion Hundorf, legal representative, Bonn (DE); Peter Ostle, Euskirchen (DE)

(73) Assignee: The Procter & Gamble Company, Cincinnati, OH (US)

(*) Notice: Subject to any disclaimer, the term of this patent is extended or adjusted under 35 U.S.C. 154(b) by 957 days.

(21) Appl. No.: 13/156,717

(22) Filed: Jun. 9, 2011

(65) Prior Publication Data
US 2011/0303354 A1    Dec. 15, 2011

(30) Foreign Application Priority Data
Jun. 9, 2010   (EP) .................................. 10165348

(51) Int. Cl.
| | | |
|---|---|---|
| *B05C 1/08* | (2006.01) | |
| *A61F 13/15* | (2006.01) | |
| *B29C 65/56* | (2006.01) | |
| *B32B 37/14* | (2006.01) | |
| *B41F 3/02* | (2006.01) | |
| *B29C 65/00* | (2006.01) | |
| *B41F 16/00* | (2006.01) | |
| *B32B 38/14* | (2006.01) | |
| *B29C 65/10* | (2006.01) | |
| *B29C 65/18* | (2006.01) | |

(52) U.S. Cl.
CPC ....... *A61F 13/15658* (2013.01); *B29C 66/8341* (2013.01); *B41F 16/002* (2013.01); *B41F 3/02* (2013.01); *B05C 1/08* (2013.01)

(58) Field of Classification Search
CPC .... B29C 65/10; B29C 66/43; B29C 66/1122; B29C 65/02; B29C 65/18; B29C 66/80; B29C 66/8167; B29C 66/83413; B29C 66/83513; A61F 13/15658; B41F 3/02; B41F 16/002
USPC ......... 156/446, 582, 708, 714, 715, 719, 767, 156/497
See application file for complete search history.

(56) References Cited

U.S. PATENT DOCUMENTS

| | | | |
|---|---|---|---|
| 4,388,056 A | | 6/1983 | Lee et al. |
| 4,904,440 A | * | 2/1990 | Angstadt ....................... 264/517 |
| 5,028,224 A | | 7/1991 | Pieper et al. |
| 5,161,283 A | | 11/1992 | Hansen |

(Continued)

FOREIGN PATENT DOCUMENTS

| | | | |
|---|---|---|---|
| EP | 0439012 A1 | * | 7/1991 |
| EP | 0467409 A1 | * | 1/1992 |

(Continued)

OTHER PUBLICATIONS

International Search Report mailed Aug. 2, 2011 (10 pages).

*Primary Examiner* — Sonya Mazumdar
(74) *Attorney, Agent, or Firm* — Laura L. Whitmer

(57) ABSTRACT

An apparatus for making a structure comprising solid material and typically a substrate, said apparatus comprising a first moving endless surface and adjacent thereto one or more stationary primary (vacuum) gas containers (chambers), at least one thereof being connected to a secondary (vacuum) gas container, whereby the pressure difference between primary and secondary containers is minimized; and methods using such an apparatus.

17 Claims, 4 Drawing Sheets

(56) References Cited

U.S. PATENT DOCUMENTS

| | | |
|---|---|---|
| 6,742,566 B2 | 6/2004 | Nishikawa et al. |
| 2003/0042660 A1 | 3/2003 | Venturino et al. |
| 2006/0021695 A1 | 2/2006 | Blessing et al. |
| 2006/0024433 A1 | 2/2006 | Blessing et al. |
| 2006/0048880 A1 | 3/2006 | Blessing et al. |
| 2008/0215166 A1 | 9/2008 | Blessing et al. |
| 2010/0224311 A1 | 9/2010 | Blessing et al. |
| 2011/0017398 A1 | 1/2011 | Blessing et al. |

FOREIGN PATENT DOCUMENTS

| | | |
|---|---|---|
| EP | 1621165 A1 * | 2/2006 |
| JP | 56-90435 U | 12/1979 |
| JP | 61-145888 | 7/1986 |
| JP | UM3107881 | 4/2005 |
| JP | 2007-202640 A | 8/2007 |
| WO | WO 03020193 A1 * | 3/2003 |

\* cited by examiner

APPARATUS AND METHOD FOR RETAINING AND RELEASING SOLID MATERIAL

FIELD OF THE INVENTION

This invention is direction to an apparatus for making a structure comprising solid material and typically a substrate, said apparatus comprising a first moving endless surface and adjacent thereto and in communication therewith one or more stationary primary (vacuum) gas containers (chambers), at least one thereof being connected to a secondary (vacuum) gas container, whereby the pressure difference between primary and secondary containers is minimized. The invention also relates to methods using such an apparatus.

BACKGROUND OF THE INVENTION

In the last decades, various processes have been proposed for making absorbent cores with fibers and/or superabsorbent polymer particles (SAP particles), also referred to as absorbent gelling polymer particles (AGM particles), including processes whereby said material is laid down on a moving surface, such as a drum surface with one or more reservoirs and held onto said surface by for example vacuum. These approaches include indirect printing methods whereby the AGM and/or fibers are taken up by a drum from one or more bulk storage(s) of said fibers and/or AGM particles, and whereby the drum then rotates towards a substrate such as a nonwoven, to then release the AGM and/or fibers onto the substrate. The drum may have one or more reservoirs, each being in the shape of a structure such as for example an absorbent (diaper) core, which is then filled with fibers and/or AGM. However, at high speed, such complete structures are difficult to transfer completely and/or accurately at high speed onto a second surface, such as a moving nonwoven web. In more recent years, it has been proposed to deposit fibers and/or AGM into smaller reservoirs. Such a multitude of smaller reservoirs may then together be in the form of a diaper core, so that when the AGM content of all the reservoirs is transferred onto a second surface, like a nonwoven web, a core is formed. This is for example described in EP-A-1621165. With such s method and apparatus an improved transfer of the solid material can be achieved; furthermore, such an apparatus and process may be used to produce absorbent cores that have a specific profile or distribution, such as a predetermined pattern, MD-, CD-, or thickness-profile, corresponding to the pattern/depth of the reservoirs. The AGM or fibers may be retained on the drum surface, in the reservoirs, by use of vacuum suction under the surface. The AGM or fibers may be removed from the drum by use of gravity, or optionally, by use of additional blow-off air, to blow the solid material of the drum surface.

The inventors found that, depending on the apparatus and process characteristics or depending on the requirements of the structures to be produced, such proposed (indirect) printing or transfer processes do not always have the desired (complete) transfer or the complete and/or accurate release of the solid material, for example at high process speeds (of more than 800 or more than 1000 parts (e.g. structures, such as absorbent cores) per minute), or for example when fine particulate material is used, or for example when the moving surface (such as a print roll or drum) comprises substantial zones extending in machine direction, MD and cross-machine direction CD) without reservoirs (for example corresponding to the zones between absorbent cores of the web of absorbent cores produced by the method or with the apparatus). The inventors found that the air flow and/or vacuum suction may be impeded in some of such instances, or that the air flow and/or vacuum may be difficult to control in some instances.

The inventor now found a new method and a new apparatus that can provide an improved reception/transfer and/or release of solid material, resulting in a more consistent or accurate transfer or deposition of the solid material, e.g. on a substrate, and hence improved absorbent core formation, said method and apparatus being more flexible in use, e.g. at a wide span of process or apparatus settings characteristics, for example even at high speeds, or even when small reservoirs am used, or even when fine particulate material is transferred.

SUMMARY OF THE INVENTION

The present invention relates to an apparatus for producing structures comprising solid material and for example a substrate, said apparatus having a first moving endless surface for receiving and/or transferring a solid material and for releasing the solid material to a second moving surface, for example being or including a substrate.

said surface having a multitude a openings for allowing gas passage; and said apparatus comprising a gas supply system for applying a gas (e.g. air) to said first moving endless surface and through said openings, for facilitating release of said solid material from said surface, whereby said gas-supply system comprises a primary gas container and a secondary gas container, connected to one another, and optionally a tertiary gas container, connected to said secondary is container, said primary gas container being adjacent said first moving endless surface and in gas-communication therewith (e.g. but the secondary gas container is not in direct gas-communication therewith) and whereby the pressure difference between the pressure in said primary gas container ($P_1$) and the pressure in said secondary gas container ($P_2$) is less than 40%, or for example less than 30%, or for example less than 25%, or for example less than 20%, or for example less than 15%; but said difference being more than 0%, e.g. at least 0.1% or a least 1%.

The pressure in said primary gas container ($P_1$) and the pressure in said secondary gas container ($P_2$) are typically both at least 1 kPa.

Said pressurized gas (e.g. air) passes through the openings of said first moving endless surface, e.g. of the reservoirs thereof, to apply gas (air) pressure onto the solid material (e.g. in said reservoirs), to aid release thereof from said first moving endless surface, e.g. from said reservoirs. (This may be herein referred to as blow-off air/blow off method step.) The solid material is then released from the reservoir(s) to for example a second moving endless surface, for example being or including a substrate, and the accurate deposition of the material on for example a second moving endless surface.

$P_1$ and $P_2$ are in some embodiments herein within the range of from 5 kPa to 15 kPa.

In some embodiment, said secondary gas container provides to said primary gas container an average air volume-flow with a volume flow rate of at least 300 Nl/min, preferably at least 400 Nl/min.

The invention also provides an apparatus for producing structures comprising solid material and typically a substrate, having a first moving endless surface for receiving and/or transferring a solid material, for example transferring it to a releasing zone, said surface having a multitude of openings for allowing gas (e.g. air) passage; and said apparatus comprising a vacuum system for applying a vacuum suction through said openings of said surface, for facilitating retention of said solid material on said surface, whereby said vacuum system comprises a primary vacuum gas container and a secondary vacuum gas container, connected to one another, and optionally a tertiary vacuum gas container, connected to said secondary vacuum gas container, said primary vacuum gas container being adjacent said first moving endless surface, (and e.g. in gas-communication herewith, but the secondary vacuum gas container not being in direct gas-communication therewith)

whereby the pressure difference between the pressure in said primary gas container ($P_{1\nu}$) and the pressure in said secondary gas container ($P_{2\nu}$) is less than 40%, or for example less than 40%, or for example less than 30% or for example less than 25% or for example less than 20% or for example less than 15%, but more than 0%; but said difference being more than 0%, (e.g. at least 0.1% or at least 1%.

The pressure in said primary vacuum gas container ($P_{1\nu}$) and the pressure in said secondary vacuum gas container ($P_{2\nu}$) are typically both −1 kPa or less.

In some embodiment, said primary gas container or primary vacuum gas container has a volume $V_1$ of less than 2.0 liter, or for example less than 1.0 liter. The secondary gas container or secondary vacuum gas container has typically a volume $V_2$ that is more than $V_1$. In some embodiments, $V_2$ is for example at least 1.3 liter, or for example at least 2.7 liter, or for example at least 3.0 liter or for example at least 3.4 liter; and for example optionally is to 15 liter.

The apparatus herein may also have a combination of said primary and secondary gas container(s) and a vacuum system, for example including and secondary vacuum gas container(s) set out above and herein after.

Typically, said first moving endless surface is a cylindrical surface, rotatably moving around a cylindrical stator and said primary gas container(s) and/or said primary vacuum gas container(s) is (are) a chamber(s) inside said stator (but the secondary gas container(s) and/or secondary vacuum gas container(s) is/are not).

A primary gas container may be connected to two or more secondary gas containers. A primary vacuum container may be connected to two row more secondary gas containers.

DETAILED DESCRIPTION OF THE INVENTION

Apparatus 1

Figure 1:
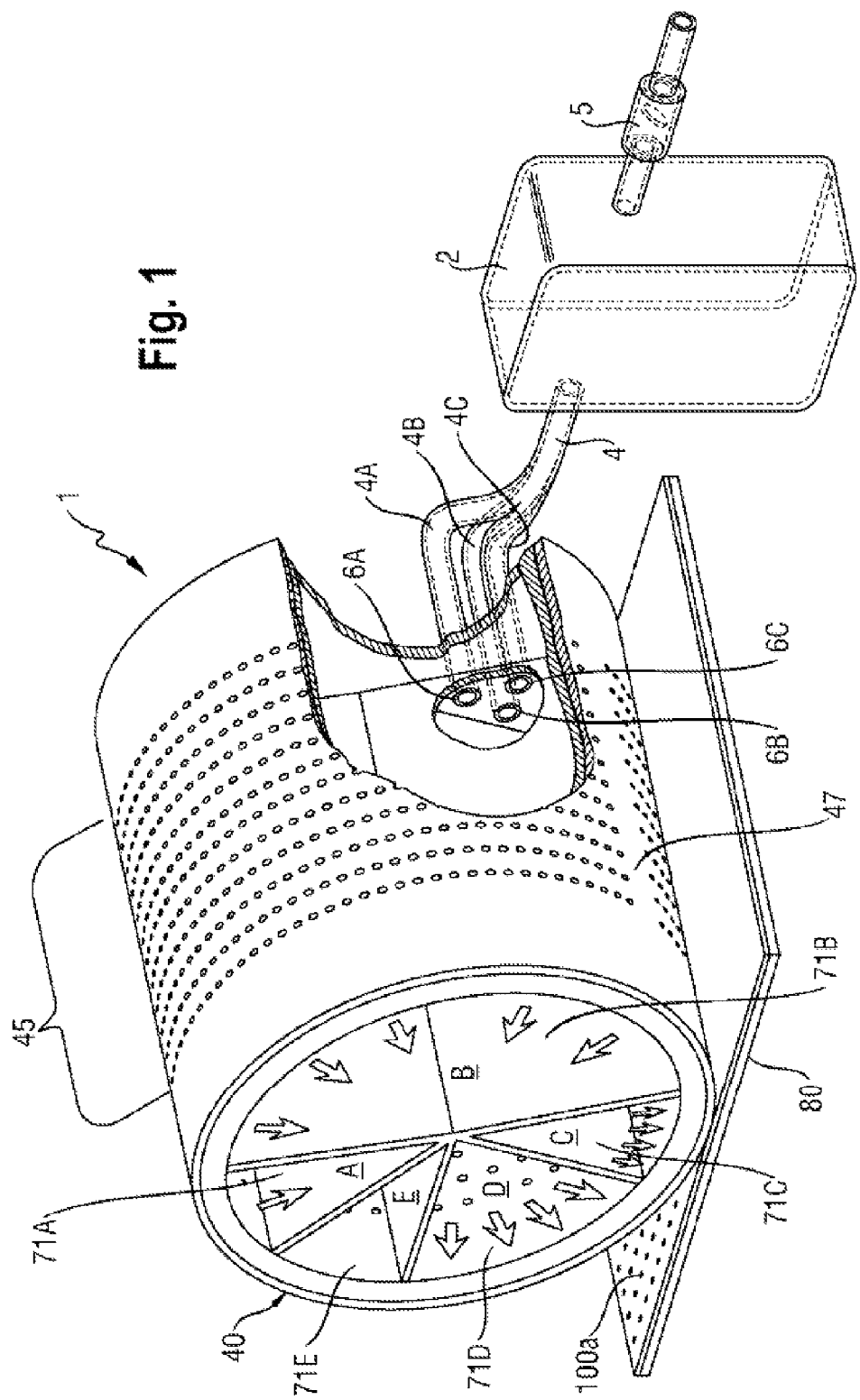
FIG. 1 shows a perspective view of an exemplary apparatus 1 of the present invention having a secondary gas container connected to a primary container.

The apparatus 1 of the invention comprises a first moving endless surface 40 for receiving and/or transferring solid (e.g. particulate) material and/or releasing it there from.

The first moving endless surface 40 has in some embodiment herein, at any point of time, a receiving zone A and/or transferring zone B and/or a releasing zone C, or for example it has each of said zones. The first moving endless surface 40 has a direction of movement (e.g. rotation), herein referred to as MD.

The first moving endless surface has openings that allow gas passage, and typically no significant solid material passage.

Also, the apparatus herein may have a receiving zone A, for receiving solid material, and/or a transferring zone B, for transferring said solid material and/or a releasing zone C for releasing said solid material, whereby the first moving endless surface 40 of the apparatus moves through said zones. Said zones may be defined by the function they have, e.g. reception of solid material in the receiving zone A, e.g. from one or more sources such as a feeder, e.g. a hopper; transfer of solid material, (for example from said reception zone and for example to the zone where it is released, in the transfer zone); release of the material, in the release zone, to for example a second moving surface 80, for example a substrate or including a substrate, as described herein after.

The method herein has corresponding method steps.

The apparatus has typically a stationary component, also referred to as stator, adjacent said first moving endless surface 40 that has a stationary receiving zone A, and/or stationary transferring zone B and stationary releasing zone C.

The apparatus of the invention, and stator thereof and first moving endless surface thereof, and the method of the invention may comprise optional additional zones, such as for example a cleaning zone D, for cleaning the moving endless surface (for example between zone C and A); the order of zones may thus for example be A-B-C-optionally D; A-B-C-optionally D; etc.

In some embodiment of the invention, the apparatus 1 comprises a gas-supply system for applying a gas to said first moving endless surface 40 (through said openings thereof), for facilitating release of said solid material from said surface 40, and said gas-supply system comprises a primary gas container(s) 71C adjacent said first moving endless surface 40 and a secondary gas container 2, that are connected to one another, and optionally a tertiary gas container, connected to said secondary gas container 2. The secondary gas container 2 may not be adjacent said first moving endless surface. The secondary gas container is typically stationary, but it is typically not contained by said stator of the apparatus that has said zone C, and zone A/B, and optional further zones. The secondary gas container is not in direct gas communication with said surface, but indirectly via said primary gas container. In some aspect of the invention, the apparatus 1 has a stationary component with a releasing zone C, including a primary gas container(s), e.g. chamber, 71C, and optionally a cleaning zone D, including optionally a further primary gas container(s), e.g. chamber, 71D.

In some other or additional aspects of the invention, the apparatus 1 comprises a vacuum system for applying a vacuum suction through said openings of said surface 40, for facilitating retention of said solid material on said surface 40 (e.g. or in the reservoirs 50 thereof). Said vacuum system may comprise one or more primary vacuum gas container 71A; 71B(s) adjacent said first moving endless surface 40, and one or more secondary vacuum gas container 3A; 3B, each connected to a single primary vacuum gas container, or each connected to a separate primary vacuum chamber, and optionally one or more tertiary vacuum gas container, connected to one or more secondary vacuum gas container 3A; 3B). The secondary gas vacuum container(s) may not be adjacent said first moving endless surface. The secondary vacuum gas container is not in direct gas communication with said surface, but indirectly via said primary vacuum gas container. The secondary gas container(s) is/are typically stationary, but it is typically not contained by said stator of the apparatus that has said zone C, and zone A/B, and optional further zones.

Thus, in some aspect of the invention, the apparatus 1 has a receiving zone A with a stationary component including a primary vacuum gas container 71A (e.g. chamber) and/or the transfer zone B with a stationary component including a primary vacuum container (e.g. chamber) 71B, described below in detail.

A primary gas container or primary vacuum gas container may be connected to two or more secondary gas containers or secondary vacuum gas container, respectively, but in some embodiments, a primary gas container or primary vacuum gas container is connected to a single secondary vacuum gas container, respectively. In some embodiments, two or more primary gas containers or primary vacuum gas containers may be connected to a single secondary gas container or secondary vacuum gas container, provided they require the same positive or negative pressure.

However, in preferred embodiments, a single gas container or primary vacuum gas container is connected one or more secondary gas containers or two or more secondary vacuum gas containers, respectively The first moving endless surface 40 herein may be any moving surface that can rotate to provide a moving endless surface, for example it may be a transporter belt or a drum or print roll, as known in the art, which can rotate and thus provide an endless surface, typically that rotates adjacent a stationary component (stator). It may be a cylindrical surface, such as drum or roll that is rotatable about a cylindrical stationary component (stator) that then contains for example said primary gas container(s) 71C (optionally 71D) and or primary vacuum gas container(s) 71A;71B.

The first moving endless surface 40 may comprise a reservoir 50 or, in preferred embodiments, a multitude of reservoirs 50 for receiving said solid material 100 therein, and that thus have a void volume that can be filled with said solid material 100.

The reservoirs 50 may have any dimensions and shape, including cubical, cylindrical, semi-spherical, conical, or any other shape. This may be any suitable number of reservoirs 50, but for example at least 20 or for example at least 50.

The reservoirs 50 may be present as identical reservoirs 50, or they may vary in dimension(s) or shape. They may be present in a pattern over the surface of said first moving endless surface 40, or they may be present uniformly over said surface. The exact number of reservoirs, reservoir pattern, dimensions etc. will depend on the required structure to be formed, but it may for example also depend on the particle size of the particulate material 100, process speed etc. In one embodiment at least 30% of the external surface area of the first moving endless surface 40 comprises said reservoirs 50, preferably at least 40% and for example up to 60%, or for example up to 55%, or for example up to 50%. If the moving endless surface has a central zone 45 described hereinafter, then these percentages may be percentages based on the surface area of the central zone, rather than the total first moving endless surface 40.

The reservoirs 50 may be present as lines of reservoirs in MD and rows in CD, (the direction perpendicular to MD). Alternatively, they reservoirs 50 may for example be present in so-called alternating rows and/or lines (whereby alternating reservoirs form a row and/or line).

The distance in MD between the centre point of a reservoir 50 (said centre point being in the plane of the outer surface of the first moving endless surface 40) and the centre point of a neighboring reservoir 50 (in a line of reservoirs) may for example be at least 3 mm, or for example at least 4 mm, or for example at least 6 mm, or for example up to 40 mm or for example up to 30 mm or for example up to 20 mm. This may apply to all such distances between neighboring reservoirs 50 in MD, or this may be an average over all such distances.

The distance in CD between the centre point of a reservoir 50 (said centre point being in the plane of the outer surface of the first moving endless surface 40) and the centre point of a neighboring reservoir 50 (in a row of reservoirs) may for example also be as above.

Said lines may extend substantially parallel to, and equally spaced from, one another and/or said rows may extend substantially parallel to, and equally spaced from, one another.

In one embodiment, the MD dimension of a reservoir 50 may be (on average over all reservoirs 50 and/or for each reservoir; measured over the outer surface of the first moving endless 40) at least 1 mm, or for example at least 2 mm, or for example at least 4 mm, and for example at the most 20 mm or for example at the most 15 mm. The CD dimension may be within the same ranges as above, or it may even be the same as the MD dimensions for one or more or each reservoir.

The reservoirs 50 may have any suitable dent dimension; the (maximum) depth may depend for example on the thickness/caliper of the desired structure to be produced, the particle size of the material, etc. The maximum depth of a reservoir 50 and/or of all reservoirs 50, and/or the average maximum depth (average over all maximum depths of all reservoirs 50) may for example be at least 1 mm, or for example at least 1.5 mm, or for example 2 mm or more, and for example up to 20 mm, or for example up to 15 mm, or in some embodiment herein, up to 10 mm, or for example up to 5 mm or for example up to 4 mm.

According to one embodiment herein, the reservoirs 50 may have a dimension in MD (average; and/or all reservoirs 50) of from 2 to 8 mm or from 3 mm to 7 mm; and the reservoirs 50 may have a maximum depth and/or average maximum depth of for example from 1.5 mm to 5 mm, or to 4 mm.

The first moving endless surface 40 may have any suitable width, but for example a width (perpendicular to MD) corresponding (substantially) to the width of the structure to be produced; this for example be a least 40 mm, or for example at least 60 mm, or for example up to 400 mm, or for example up to 200 mm. It may be useful that the moving endless surface 40 has opposing lateral zones and a central zone 45 therein between, along the whole surface in MD, and said reservoirs 50 are only present in said central zone 45. Then, the width dimensions of the surface may apply to the width of the central zone 45 instead.

In some embodiments herein, the first moving endless surface 40 has a IMD-extending and CD-extending zone(s) 47 that comprises no reservoirs 50, e.g. a CD-extending zone of at least 2 times, or for example at least 3 times the dimension (in MD) of the average reservoir dimension (in MD); such reservoir free zone(s) 47 may be positioned between a the front edge of the reservoir(s), or row of reservoirs that correspond to the front edge of a structure to be produced and the back edge of the reservoir(s) or row of reservoirs that correspond to the back edge of the same or a neighboring structure to be produced by the apparatus 1. The presence of such a reservoir-free zone (47) results (after release of the solid material from the first moving endless surface 40, for example onto a second moving surface 80, e.g. substrate) into a zone on said second moving surface, e.g. substrate, that is free of said solid material. This may then be a zone where the substrate may be cut to separate the articles produced by the apparatus 1 and method herein.

It should be understood that for purpose of determination of properties of the first moving endless surface 40 (such as the MD, the radius, the width of said first moving endless surface 40, the surface, area of, or with, the reservoirs . . . ) the surface area between reservoirs is used for such determinations. This surface area between reservoirs is herein referred to as "outer surface area" of said first moving endless surface.

The first moving surface comprises openings to allow gas passage (flow) there through, e.g. to allow vacuum suction, and/or to allow pressurized air (bow-off air) there through. Thus, the first moving endless surface, e.g. at least the reservoirs 50 thereof, is/are directly or indirectly connectable or connected to said primary gas container(s) 71C; 71D and/or said primary vacuum gas container(s) 71A; 71B. Typically, the reservoirs 50 of the surface comprise thereto a bottom surface area with one or more openings that ensure that the reservoirs 50 are in gas (air) communication with said primary gas container 71C and/or primary vacuum gas container(s) 71A;71B. Typically each reservoir 50 has at least one such opening that is connected or connectable to said primary gas container(s) 71C; 71D and/or said primary vacuum gas container(s) 71A; 71B.

The radius of the first moving endless surface 40 may depend on what structure is produced, and what size of structure is produced, and for example how many structures are produced per cycle of the first moving endless surface 40, e.g. drum. For example, the first moving endless surface may have a radius of at least 40 mm, or of at least 50 mm; it may be for example up to 300 mm, or for example up to 200 mm.

The primary gas container(s) 71C; 71D and/or the primary vacuum gas container 71A;71B adjacent the moving endless surface 40 (e.g. contained by the stator) are typically of a small volume, for example due to the limited radius of the moving endless surface 40 and e.g. hence of the stator.

Furthermore, the surface area where solid material 100 is received by the moving surface 40, the receiving zone A, may be small, and hence the primary vacuum as container(s) 71A may have a small surface area that is adjacent (coincides) with the (internal) surface are of the first moving endless surface in zone A, adjacent said surface in said receiving zone A. The same may apply to the transfer zone B and possible primary vacuum gas container 71B in said zone adjacent said surface in said zone.

Alternatively, or in addition, the releasing zone C, where solid material is released from the moving endless surface 40, e.g. onto a substrate, is typically small, and hence the primary gas container may have a small surface area that is adjacent (coincides) with the (internal) surface area of the first moving endless surface 40 adjacent said surface in said releasing zone C. The same may apply to the optional cleaning zone D.

For example the primary gas container(s) 71C; 71D and/or primary vacuum gas container(s) 71A;71B may each have a volume $V_1$ of less than 2.0 liters, or alternatively, less than 1.5 liter, or for example less than 1.0 liter or for example less than 0.7 liter or for example less than 0.5 liter. In particular the primary gas container 71C in the releasing zone C and/or the primary vacuum gas container 71A in the receiving zone A may have a volume $V_1$ of less than 1.0 liter.

In order to ensure a improved gas flow to and through the moving endless surface 40, i.e. the openings therein, the apparatus 1 of the invention, in one aspect thereof, comprises one or more secondary gas container(s) 2 connected to said primary gas container 71C, typically connected via a gas inlet tube 4 described below, and optionally secondary gas container(s) 2B connected to a primary gas container in zone D, 71D. The pressure in the primary gas container ($P_1$) and the pressure in (each) said secondary gas container, ($P_2$), may each be required to be a least 1 kPa, or for example at least 2 kPa, or for example at least 3 kPa, or for example at least 4 kPa, or for example at least 5 kPa, and for example up to 40 kPa or for example up to 20 kPa.

The pressure difference between the pressure in said primary gas container ($P_1$) and the pressure said secondary gas container ($P_2$) that are connected to one another is less than 40%, or for example less than 30%; or for example less 25% or; in some embodiments herein less than 20% or for example less than 10%; however, in order to ensure gas flow, the pressure difference between $P_2$ and $P_1$ has be more than 0%, for example at least 0.1% or for example at least 1.0%.

The pressure in said tertiary gas container ($P_3$), if present, may be within the range at set out above and the pressure difference between the pressure in said secondary gas container ($P_2$) and the pressure in said tertiary gas container ($P_3$), if present, may be as set out above.

In another or alternative aspect of the invention, and in order to ensure an improved gas flow to and through the first moving endless surface 40, e.g. the openings therein, the apparatus 1 of the invention comprises one or more secondary vacuum gas container 3A; 3B, (each) connected to one or more of said primary vacuum gas container(s), typically via a gas inlet tube 4. The vacuum pressure in a primary gas container ($P_{1v}$) and the vacuum pressure in a secondary vacuum gas container, ($P_{2v}$), may be required to be a vacuum pressure of −1 kPa or less; or for example of −2 kPa or less; or for example −3 kPa or less; or −4 kPa or less; or −5 kPa or less; and for example −40 kPa or more, or for example −30 kPa or more.

The pressure in said primary vacuum gas container ($P_{1v}$) and the pressure in said secondary vacuum gas container ($P_{2v}$) are both such that the pressure difference between the pressure in said primary vacuum gas container ($P_{1v}$) and the pressure in said secondary vacuum gas container ($P_{2v}$), that are connected to one another, is less than 40%; or for example less than 30%; or for example less than 25%; or, in some embodiments herein less than 20%; or for example less than 10%. However, in order to ensure gas flow the pressure difference between $P_{2v}$ and $P_{1v}$ has to be more than 0%; for example at least 0.1%, or for example at least 1.0%.

The pressure in a tertiary vacuum gas container ($P_{3v}$), if present, may be in the range as set out above for the primary vacuum chamber and the pressure difference between the pressure in said secondary vacuum as container ($P_{2v}$) and the pressure in said tertiary gas vacuum container ($P_{3v}$), if present, may be less than 40%, or for example less than 30% or for example less than 25% or, in some embodiments herein less than 20% or for example less than 10%.

The pressure in the primary/secondary (vacuum) gas containers herein can be measured by use of a BD sensor, available from BD Sensors GmbH (www.bdsensors.com); for example for the measurement of the positive gas pressures of the gas containers herein and differences between those pressures, a BD sensor model 0-10V OUT; 0-0.4 Bar; M12×14P G1/4 is used; for example for the negative vacuum pressures of the vacuum gas containers herein and differences thereof can be measured with a BD sensor model 0-10V OUT; 0 to −0.4 Bar; M12×14P G1/4 is used. The negative and/or positive pressures are measured at 20° C. The sensors are set with as reference the surrounding, e.g. atmospheric pressure, this being set as 0 kPa.

The sensor is positioned outside a (vacuum) gas container, but connected to the gas container with a 20 cm long Festo tube, with a 10 mm diameter, mounted in the gas container.

It may be beneficial that the secondary (vacuum) gas container has a volume $V_2$ that is more than the volume $V_1$ of the connected primary (vacuum) gas container, or in the event two or more one secondary (vacuum) gas container are connected to a primary gas container, the combined volume of the secondary gas containers or secondary vacuum gas containers is $V_2$ and this is s more than $V_1$; optionally when present, said tertiary (vacuum) gas container has a volume $V_3$ that is more than $V_1$.

It may be beneficial that the $V_2$ is at least 1.3 liter, or for example at least 2.7 liter, or for example at least 3.4 liter, or for example at least 4.0 liter, and for example depending on the apparatus 1 dimensions and restrictions, optionally up to 30 liter, or to 20 liter or to 15 liter. If present, the tertiary gas container may have a volume $V_3$ within said ranges.

Said secondary gas container(s) 2 may provide to said primary gas container 71C connected thereto, an average gas (e.g. air) volume-flow of a rate of at least 300 Nl/min, or for example at least 400 Nl/min. Furthermore, if present, the tertiary gas container may provide to said secondary gas container(s) 2 an average gas (e.g. air) volume-flow of at least 300 Nl/min, or for example at least 400 Nl/min.

The average gas (e.g. an) volume-flow from a primary vacuum gas container 71A; 71B to a connected secondary vacuum gas container(s) 3; 3B may be at least 300 Nl/min, or for example at least 400 Nl/min, or for example at least 500 Nl/min, or for example at least 100 Nl/min or for example at least 1500 Nl/min.

The as volume flow rate is measured with a Probe ZS25 ZG4; (available from Höntzsch GmbH.

Gottlieb-Daimler-Str. 37, Waiblingen, Germany); this is positioned such that it measures the now accurately and does not impede the flow, for example in the gas flow regulator 5, described herein after, or in or in close proximity to the gas inlet a the secondary gas container or secondary vacuum gas container, e.g. where the gas inlet tube(s) enter the secondary (vacuum) gas container.

Figure 5:
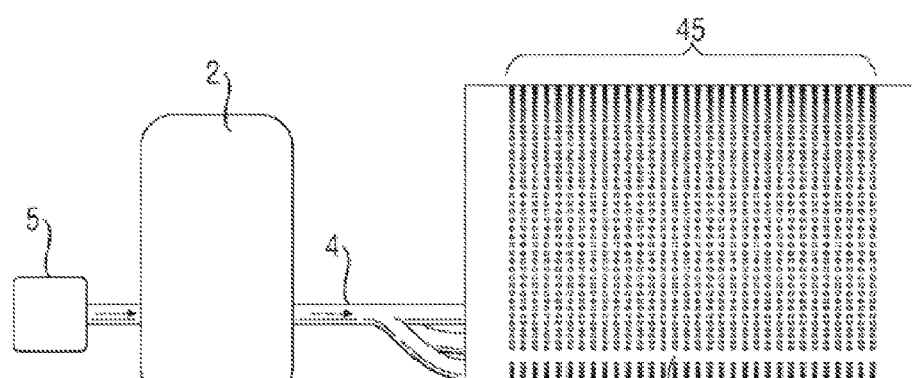
FIG. 5 shows a side view of an apparatus 1 of the present invention, for example the apparatus of FIG. 3, showing a primary gas container and a secondary gas container.

The apparatus 1 typically comprises a gas (e.g. air) flow regulator 5 that can regulate the airflow to said secondary gas container 2; 2B. The gas flow regulator 5 is typically placed before the secondary gas container 2; 2A, and not between the primary and secondary (vacuum) gas container in order not to negatively impact the gas pressure of the primary and secondary gas containers and difference thereof, as is for example shown in FIGS. 3 and 5.

The gas flow regulator 5 may be operationally connected to the pressure sensor described above, so that for example the output signal of the sensor of the primary gas container can be the input signal for the regulator.

In addition, or alternatively, the secondary vacuum gas container 3A; 3B may also be connected to a gas flow regulator 5, and this may also be operationally connected to the pressure sensor of the primary vacuum gas container 71A; 71B.

Figure 2:
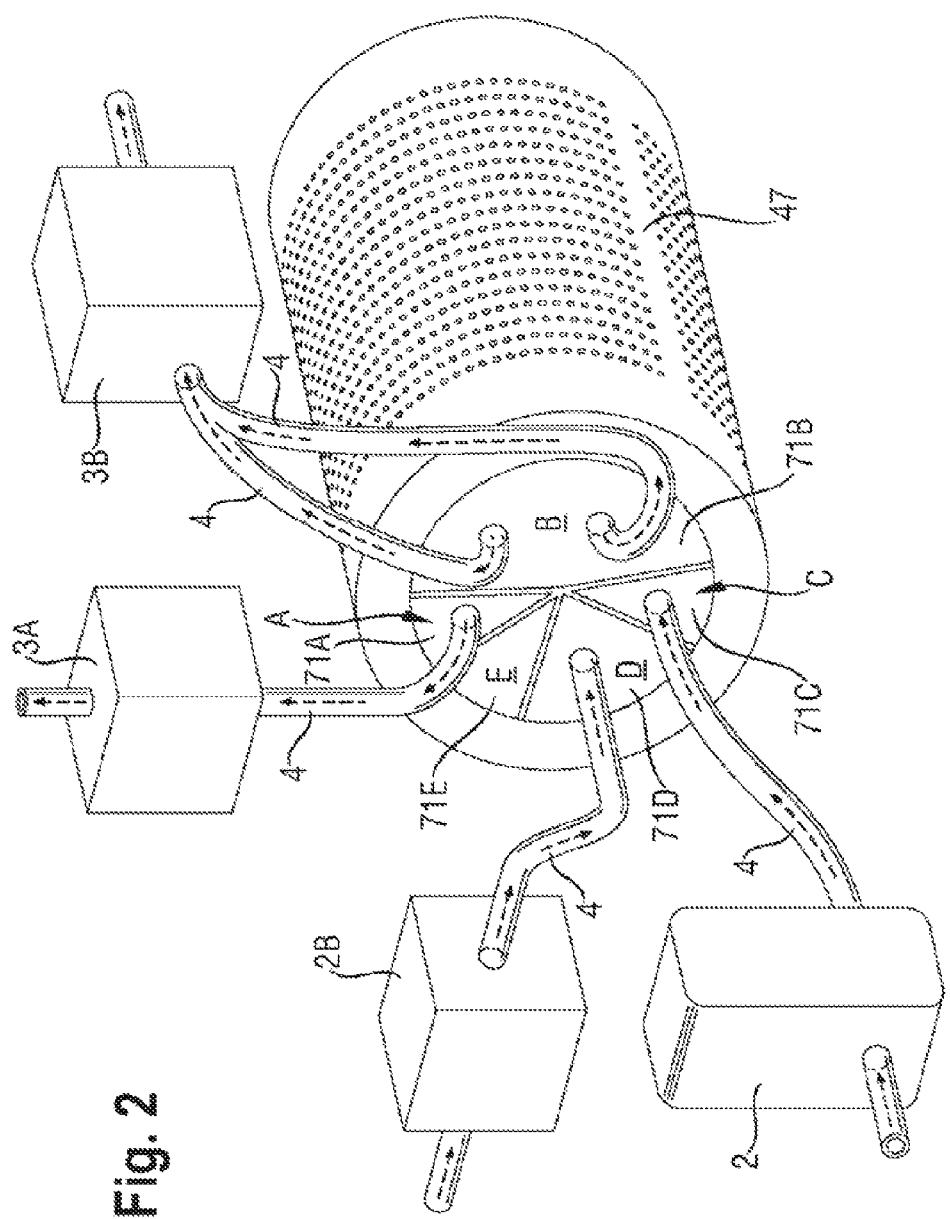
FIG. 2 shows a perspective view of an exemplary apparatus 1 of the present invention having primary gas containers each connected to a secondary gas container and having primary vacuum gas containers each connected to a secondary vacuum gas container.
Figure 3:
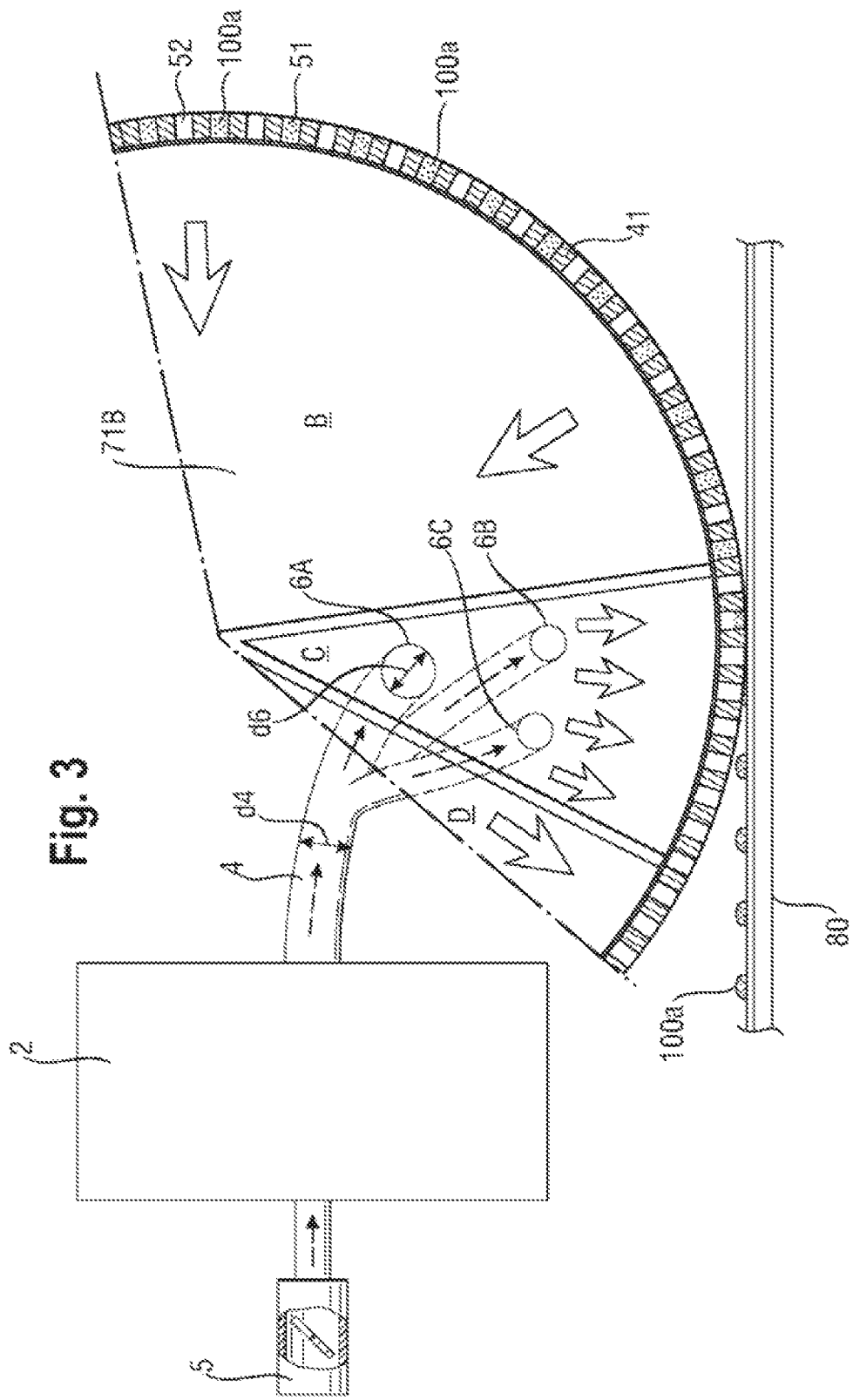
FIG. 3 shows a cross-sectional partial view of an apparatus 1 of the present invention, showing a primary gas container and a secondary gas container.
Figure 4:
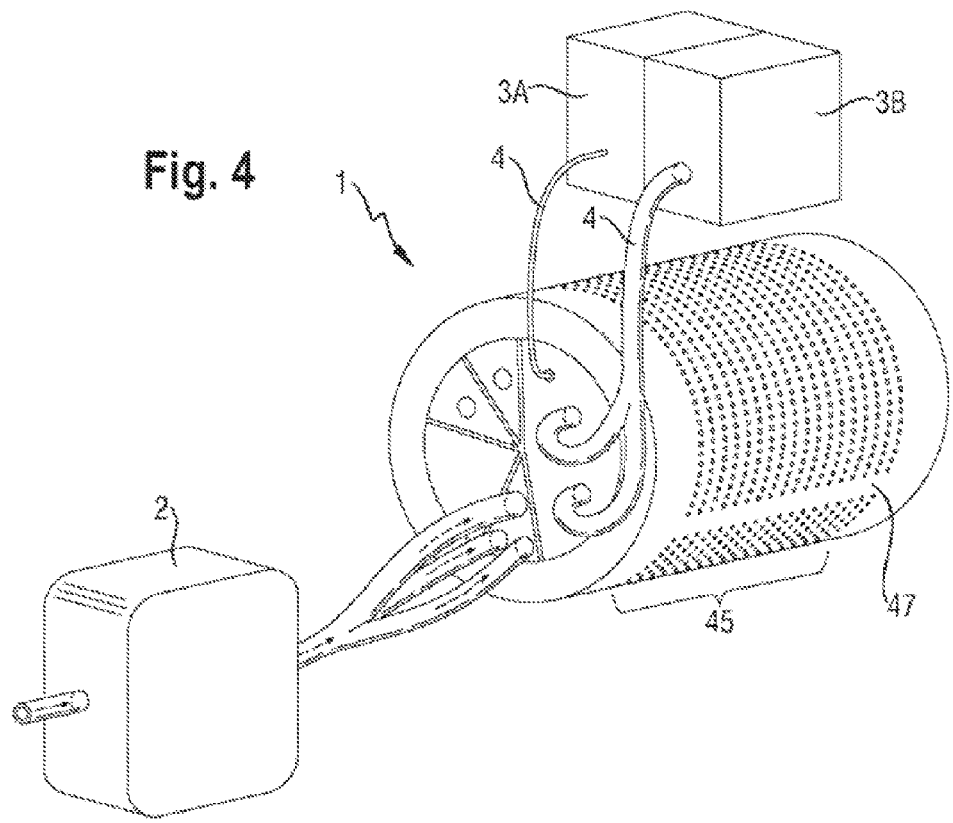
FIG. 4 snows a perspective view of an exemplary apparatus 1 of the present invention having a primary gas container connected to a secondary gas container and having a primary vacuum gas container connected to secondary vacuum gas containers.

The gas (e.g. air) may enter said primary gas container 71C; 71D via one or more as inlet(s) 6A; 6B; 6C, that may be connected to one or more gas inlet tube(s) 4 for example shown in FIGS. 1, 2 and 3. Said gas inlet tube(s) 4 are then connected to said secondary gas container or containers 2; 2B, typically directly connected thereto.

In some embodiments, there may be two or more, or three or more gas inlets 6A; 6B; 6C in said or each of said primary gas container 71C; 71B. Said two or more gas inlets 6A; 6B; 6C may be connected with two or more gas inlet tubes 4 to said secondary gas container 2, or for example, each of said the two or more gas inlets 6A; 6B; 6C may each be connected to a gas inlet tube 4, and then said two or more gas inlet tubes 4 join prior to being connected as a single gas inlet tube to said secondary gas container 2, as for example shown in FIG. 1. In some other embodiments, there may be a single gas inlet 6A in said primary gas container 71C and for example a single gas inlet tube 4 connecting said primary gas container 71C and secondary gas container, as for example shown in FIG. 2 (with respect to gas container 71C, and in additional optionally also with respect to gas container 71D).

In some embodiments, there may be two or snore, or three or more gas inlets 6A; 6B; 6C in said or each of said primary vacuum gas container 71A; 71B. Said two or more gas inlets 6A; 6B; 6C may be connected with two or more gas inlet tubes 4 to said secondary vacuum gas container 3A;3B, or for example, each of said two or more gas inlets 6A; 6B; 6C may each be connected to a gas inlet tube 4, and said two or more gas inlet tubes 4 join prior to being connected (as a single gas inlet tube 4) to said secondary vacuum gas container 3; 3B, as for example shown in FIG. 2, with respect to vacuum chamber 71B. In some other embodiments, there may be a single gas inlet 6A in said primary vacuum gas container(s) 71A; 71B and for example a single gas inlet tube 4 connecting a primary vacuum gas container 71A;71B and a secondary vacuum gas container 3A; 3B, as for example shown in FIG. 2, with respect to vacuum chamber 71A.

In some embodiments herein, it may be beneficial to maximize the surface area of a gas inlet; it may be that said gas inlet has a cross-sectional-surface area (i.e. at the inlet point of the primary gas (vacuum) container 71C;71A; 71B of at least 100 $mm^2$ or for example at least 300 $mm^2$, or for example at least 500 $mm^2$. For the embodiment that more than one gas inlet 6A; 6B; 6C is present in a (vacuum) gas container the total cross-sectional-surface area of all gas inlets 6A; 68; 6C of a (vacuum) gas container (i.e. at the inlet, points of the primary gas container) is for example at least 100 $mm^2$, or for example at least 300 $mm^2$, or for example at least 500 $mm^2$.

The same may apply to the gas inlet or inlets of the secondary gas container and/or secondary vacuum gas container.

The gas inlet tube or tubes 4 may (each) have a cross sectional dimension, or average cross-sectional dimension that is for example at least 50 $mm^2$, or for example at least 100 $mm^2$, for example at least 300 $mm^2$, or for example at least 500 $mm^2$.

The maximum distance D from a (or each) primary (vacuum) gas container to a secondary (vacuum) gas container connected thereto may be kept to a minimum, for example the maximum distance D (from a gas inlet or each gas inlet in said primary (vacuum) gas container to a gas inlet or each gas inlet of said secondary (vacuum) gas container) may be less than 12 meters, preferably less than 5 meters, or for example less than 2 meters, or for example less than 1 meter, or for example less than 50 cm. The secondary (vacuum) gas container may in some embodiments be about adjacent the first moving endless surface, but not in direct gas communication with the surface and not present in said stator.

The solid, e.g. particulate, material 100 may be introduced on the first moving endless surface 40 (e.g. the reservoirs 50 thereof) from a feeder with an opening positioned adjacent the first moving endless surface 40. The feeder may have any form or shape. The feeder may have a container portion, to hold the material 100, e.g. having a volume of at least 1000 cm$^3$, and a guiding portion, e.g. a pipe-shapes portion, having one or more walls defining an opening that guides the material from the container portion to the first moving endless surface 40.

The average distance between the opening of the feeder and said first moving endless surface 40 may be for example less than 10 cm, or for example less than 5 cm, and it may for example be less than 2 cm or for example less than 1 cm, and for example at least 0.1 mm, or for example at least 1 mm.

The feeder may positioned above said first moving endless surface 40, for allowing gravity to help to "feed" said particulate material 100 to said first moving endless surface 40. Hereto, an opening edge of the feeder may be positioned exactly above the first moving endless surface 40 (0°), or, when the first moving endless surface 40 is curved, or even for example circular, as shown in the figures, it may be positioned above said surface, which means at any position between 90° and −90° (e.g. between 9 o'clock and 3 o'clock position), or in one embodiment between 60° and −60°, or between 30° and −30°. The receiving zone A may thus be within said positions.

The solid material 100 herein may be any material in particulate form, e.g. flowable in dry state, which includes particles, flakes, fibers, spheres, agglomerated particles and other forms known in the art.

In one embodiment herein, the solid material 100 is particulate superabsorbent material, and this material is typically polymeric, and also known as particulate (super) absorbent gelling material, herein referred to as AGM. This refers to polymeric materials in particulate form that can absorb at least 10 times their weight of a 0.9% saline solution, i.e. having a CRC value of at least 10 g/g as measured using the Centrifuge Retention Capacity test of EDANA (European Disposables and Nonwovens Association), test method No. 441.2-02 "Centrifuge retention capacity". The particulate AGM herein may have a high sorption capacity, e.g. having, a CRC of for example at least 20 g/g, or for example at 30 g/g. Upper limits may for example be up to 150 g/g, or for example up to 100 g/g.

In one embodiment herein the polymers of said AGM are internally cross-linked and/or surface crosslinked polymers. In one embodiment herein, the particulate material herein is superabsorbent material comprising or consisting of particles of polyacrylic acids/polyacrylate polymers, for example having a neutralization degree of from 60% to 90%, or about 75%, having for example sodium counter ions, as known in the art, e.g. surface crosslinked and/or internally crosslinked and/or post-crosslinked polyacrylic acid/polyacrylate polymers.

In one embodiment herein, the solid material 100 is in the form of particles with, a mass medium particle size up to 2 mm, or even between 50 microns and 2 mm or to 1 mm, or preferably from 100 or 200 or 300 or 400 or 500 µm, or to 1000 or to 800 or to 700 µm; as can for example be measured by the method set out in for example EP-A-0691133. In one embodiment of the invention, the particulate material 100 is in the form of particles with particle sizes between 50 µm and 1200 µm and a mass median particle size between any of the range combinations above. In addition, or in another embodiment of the invention, said particles are essentially spherical. In yet another or additional embodiment of the invention the particulate material 100 has a relatively narrow range of particle sizes, e.g. with the majority (e.g. at least 80% or preferably at least 90% or even at least 95%) of particles having a particle size between 50 µm and 1000 µm, preferably between 100 µm and 800 µm, and more preferably between 200 µm and 600 µm.

The particulate material 100 herein may advantageously comprise less than by 15% by weight of water, or for example less than 10%, or for example less than 8% or for example less than 5%. The water-content can be determined by the Edana test, number ERT 430.1-99 (February 1999) which involves drying me particulate material 100 at 105° Celsius for 3 hours and determining the moisture content by the weight loss of the particulate material 100 after drying.

The particulate AGM herein may be particles of AGM that are surface coated or surface treated (this not including surface-crosslinking, which may be an additional surface-modification step, not considered herein a coating or surface treatment but a surface modification); such coatings and surface treatment steps are well known in the art, and include surface treatment with one or more inorganic powders, including silicates phosphates; coatings with organic (non-polymeric) powders; and coatings of polymeric material, including elastomeric polymeric materials, or film-forming polymeric materials.

The solid material 100 is for example transferred by the first moving endless surface 40 to a second moving endless surface 80. This may be for example a belt, or drum, or this may for example be a moving substrate, or a combination thereof. The substrate may be a web material; the substrate may include a film, e.g. a film web, and/or a woven web, and/or in some preferred embodiments herein, it may include or be a nonwoven e.g. nonwoven web. The second moving endless surface may for example be a combination of a substrate carried on a moving endless surface support, such as a drum or belt. The support, or drum or belt, may comprise a vacuum system to retain the solid material and/or substrate on said support the (e.g. absorbent) structure producible with the apparatus 1 and method of the invention may thus comprise a substrate and said solid material, and optionally additional component(s)/material(s).

The second moving endless surface 80 may have the same surface speed as the first moving endless surface 40, or it may have a different speed. In one embodiment, the first and/or second endless moving surface may have a speed of at least 1000 part per minute, and/or a speed of at least 4.5 m/s, or for example at least 6 m/s, or for example at least 8 m/s.

In one embodiment, the first moving endless surface 40 rotates and the second moving endless surface 80 is for example placed positioned substantially under the first moving endless surface 40 so that the solid material 100 is released thereon aided by gravity. The release zone C may thus start at point on a line of gravity, or under an angel therewith from 60° to −60°, or from 30° to −30°.

In one embodiment herein, the substrate is a nonwoven, e.g. a nonwoven web; nonwoven, when used herein, refers to a manufactured sheet or web of directionally or randomly orientated fibers, bonded by friction, and/or cohesion and/or adhesion, excluding paper and products which are woven, knitted, tufted, stitch-bonded. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments and twisted bundles of continuous filaments (yarn). The fibers may be bicomponent fibers, for example having a sheet-core arrangement, e.g. with different polymers forming the sheet and the core. Nonwoven fabrics can be formed by many processes such as meltblowing, spun-bonding solvent spinning, electrospinning, and carding. The basis weight of nonwoven fabrics is usually expressed in grams per square meter (gsm). The substrate may be a laminate of for example a film layer and one or more nonwoven layers (nonwoven laminate), or as nonwoven laminated of two or more nonwoven layers.

The nonwoven herein may be made of hydrophilic fibers; "Hydrophilic" describes fibers or surfaces of fibers, which are wettable by aqueous fluids (e.g. aqueous both fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The substrate herein may be air-permeable. The nonwovens (webs) may have for example an air-permeability of from 40 or from 50, to 300 or to 200 m$^3$/(m$^2$×min), as determined by EDANA method 140-1-99 (125 Pa, 38.3 cm$^2$). The substrate may alternatively have a lower air-permeability, e.g. being non-air-permeable, to for example be better detained on a moving surface comprising vacuum. Films useful herein may comprise micro pores.

In certain executions, the substrate is a nonwoven web, for example laminate of the SMS or SMMS type.

The substrate may have a CD-extensibility and/or a MD-extensibility, for example of more the 20%, for example more than 100%, but for example not more than 200%. The ratio of MD-extensibility to the CD-extensibility is at a given load not more than one to two.

The substrate may comprise an adhesive, in order to, at least partially, adhere the solid material 100 to the substrate. In order to better allow vacuum to be applied on the substrate with adhesive, the adhesive may be applied in a pattern, whereby parts of the substrate do not comprise adhesive and parts of the substrate do comprises adhesive.

After transfer of the solid material 100 to the second moving endless surface, said surface may move the solid material 100 to further additional unit(s), which may be part of the apparatus 1 of the present invention, to apply further materials to the solid material 100 and/or the substrate, and the related process steps may be part of the method/process of the invention. This may include one or more (further) adhesive(s), for example applied by a further adhesive unit, and/or a further substrate applied for example by a further rotating support carrying a further substrate, a cutting unit etc. In one embodiment, after release of the solid material 100 to said substrate, the substrate moves to a unit that applies an adhesive material, and/or a thermoplastic material and/or an adhesive thermoplastic material, for example in fibrous form, to cover the solid material 100, or an thereof. In another or additional embodiment, the substrate with solid material moves to a unit that applies a further substrate onto the solid material 100, or optionally onto said adhesive and/or thermoplastic and/or thermoplastic adhesive material. Said further substrate may comprise adhesive on the side that contacts the solid material 100 (or optionally said thermoplastic and/or adhesive and/or thermoplastic adhesive material), to better adhere said substrate to said solid material 100. The substrate may be joined to itself or to a further substrate or a cover sheet by any means, for example by ultrasonic bonding, thermo-bonding or adhesive-bonding, e.g. for example sprayed adhesive bonding. The bonding region may for example be at least 1%, or for example at least 2%, or for example at least 5%, but for example not more than 50% or no more than 30% of the surface area of the substrate (110). Preferably, the bonding region comprises essentially no particulate material 100.

The resulting substrate with particulate material may thus be a web of structures herein and it may then move to a cutting unit, that cuts the web of structures into individual structures, e.g. absorbent cores for absorbent articles, or partial absorbent articles. Such absorbent cores or partial absorbent articles may then be combined with further absorbent article components, to form a final absorbent article.

Method

The present invention also relates to methods, using the apparatus 1 as described above and as claimed herein. Any of the above described features of the apparatus 1 apply the methods of the invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for making a structure comprising a solid material and a substrate, said apparatus having a first moving endless surface for receiving or transferring a solid material and for releasing the solid material to a second moving surface, said surface having a multitude of openings for allowing gas passage; and said apparatus comprising a gas-supply system for applying a gas to said first moving endless surface and through said openings, for facilitating release of said solid material from said surface, wherein said gas-supply system comprises a primary gas container and at least one secondary gas container, connected to said primary gas container, said primary gas container being adjacent said first moving endless surface and in gas communication therewith; and wherein the pressure difference between the pressure in said primary gas container ($P_1$) and the pressure in said secondary gas container ($P_2$) is more than 0% and less than 40%; and wherein the pressure in said primary gas container ($P_1$) and the pressure in said secondary gas container ($P_2$) are both at least 1 kPa.

2. An apparatus making a structure comprising a solid material and a substrate having a first moving endless surface for receiving or transferring a solid material said surface having a multitude of openings for allowing gas passage; and said apparatus comprising a vacuum system for applying a vacuum suction through said openings of said surface, for facilitating retention of said solid material on said surface, wherein said vacuum system comprises a primary vacuum gas container and one or more secondary vacuum gas container, connected to said primary vacuum gas container, said primary vacuum gas container being adjacent said first moving endless surface and in gas communication therewith;

wherein the difference between the pressure in said primary vacuum gas container ($P_{1v}$) and the pressure in said secondary vacuum gas container ($P_{2v}$) is more than 0% and less than 40%; and wherein the pressure in said primary vacuum gas container ($P_{1v}$) and the pressure in said secondary vacuum gas container ($P_{2v}$) are both −1 kPa or less.

3. An apparatus according to claim 1, comprising a solid material receiving zone A or solid material transferring B, that comprises a vacuum system for applying a vacuum suction through said openings of said surface, for facilitating retention of said solid material on said surface, wherein said vacuum system comprises a primary vacuum gas container and one or more secondary vacuum gas container, connected to said primary vacuum gas container, and said primary vacuum gas container being adjacent said first moving endless surface and in gas communication therewith, and wherein the pressure difference between the pressure in said primary vacuum gas container ($P_{1v}$) and the pressure in said secondary vacuum gas container ($P_{2v}$) is more than 0% and less than 40%.

4. An apparatus according to claim 1, wherein said primary gas container or primary vacuum gas container has a volume $V_1$ of less than 2.0 liter.

5. An apparatus according to claim 1, wherein said secondary gas container or said secondary vacuum gas container has a volume $V_2$ that is more than the volume $V_1$, and $V_2$ being at least 1.3 liter.

6. An apparatus according to claim 5, wherein $V_2$ is at least 3.0 liter and up to 15 liter.

7. An apparatus according to claim 1, wherein $P_1$ and $P_2$ are within the range of from 5 kPa to 15 kPa.

8. An apparatus according to claim 1, wherein average gas volume-flow rate of the gas flow between a primary gas container and a secondary gas container, connected thereto, or between a primary vacuum gas container and a secondary vacuum gas container connected thereto is at least 300 Nl/min.

9. An apparatus according to claim 1, wherein the maximum distance D from said primary gas container to said secondary gas container connected thereto, or from said primary vacuum gas container to said secondary vacuum gas container connected thereto, is less than 2 meters.

10. An apparatus according to claim 1, wherein said secondary gas container or said primary gas container; or said primary vacuum gas container or said secondary vacuum gas container, have one or more gas inlets, having a cross-sectional-surface area of at least 100 $mm^2$.

11. An apparatus according to claim 1, wherein said first moving endless surface is a cylindrical surface, rotatably moving around a cylindrical stator and said primary gas container or said primary vacuum gas container is a chamber contained by said stator.

12. An apparatus according to claim 11, wherein said first moving endless surface comprises a multitude of reservoirs with a void volume for retaining said solid material therein and releasing it therefrom; and each of said reservoirs having one or more of said openings, which are connected or connectable to said primary gas container or primary vacuum gas container, wherein at least 30% of the external surface area of the first moving endless surface, comprises said reservoirs.

13. A method for receiving or transferring a solid material, or for receiving or transferring and releasing a solid material to a second moving endless surface, or combination thereof, using the apparatus of claim 1.

14. A method according to claim 13, wherein said solid material is a particulate material with particles of a mass medium particle size up to 2 mm.

15. A method according to claim 13, wherein said first moving endless surface has a surface speed of at least 4.5 m/s.

16. An apparatus according to claim 1, further comprising a tertiary vacuum gas container connected to said secondary vacuum gas container.

17. An apparatus according to claim 2, further comprising a tertiary vacuum gas container connected to said secondary vacuum gas container.

* * * * *